US009045715B2

United States Patent
Josten et al.

(10) Patent No.: US 9,045,715 B2
(45) Date of Patent: Jun. 2, 2015

(54) PROCESS FOR PURIFYING CRUDE FATTY ALCOHOLS

(75) Inventors: Horst Josten, Düsseldorf (DE); Pepa Dimitrova, Kaiserslautern (DE); Truc Tran Anh, Düsseldorf (DE)

(73) Assignee: Cognis IP Management GmbH, Duesseldorf (DE)

( * ) Notice: Subject to any disclaimer, the term of this patent is extended or adjusted under 35 U.S.C. 154(b) by 286 days.

(21) Appl. No.: 13/470,283

(22) Filed: May 12, 2012

(65) Prior Publication Data

US 2012/0289724 A1 Nov. 15, 2012

Related U.S. Application Data

(60) Provisional application No. 61/485,825, filed on May 13, 2011.

(51) Int. Cl.
| | | |
|---|---|---|
| C11C 1/00 | (2006.01) | |
| C07C 29/132 | (2006.01) | |
| C07C 29/86 | (2006.01) | |
| C11C 1/02 | (2006.01) | |

(52) U.S. Cl.
CPC .............. *C11C 1/00* (2013.01); *C07C 29/132* (2013.01); *C07C 29/86* (2013.01); *C11C 1/025* (2013.01)

(58) Field of Classification Search
CPC ...... C07C 51/42; C07C 51/412; C07C 29/86; C07C 29/132; C11B 13/00; C11B 13/02; C11B 1/025
See application file for complete search history.

(56) References Cited

U.S. PATENT DOCUMENTS

| | | | | |
|---|---|---|---|---|
| 4,100,181 A | * | 7/1978 | Phillips et al. | 554/155 |
| 5,138,106 A | * | 8/1992 | Wilmott et al. | 568/877 |
| 5,157,168 A | * | 10/1992 | Wilmott et al. | 568/877 |
| 6,399,802 B2 | * | 6/2002 | Reaney | 554/179 |

FOREIGN PATENT DOCUMENTS

GB 825359 * 7/1959

OTHER PUBLICATIONS

Kreutzer, U., Manufacture of Fatty Alcohols Based on Natural Fats and Oils, 1984, JAOCS, vol. 61, No. 2. pp. 343-348.*
Annison, E.F., et al., The metabolism of short-chain fatty acids in sheep: Formic, n-valeric and some branched-chain acids, 1954, Biochem. J., vol. 57, pp. 685-692.*
Lynden, B. T., et al., Short chain fatty acids and their receptors: New metabolic targets, 2013, Translational Research, 161(3), pp. 131-140.*

* cited by examiner

*Primary Examiner* — Yate K Cutliff
(74) *Attorney, Agent, or Firm* — Servilla Whitney LLC

(57) ABSTRACT

Described is a process for simultaneously purifying fatty alcohols and obtaining a fraction of free fatty acids, wherein: (a) crude fatty alcohols comprising up to 70% b.w. alkyl esters and/or wax esters are treated with alkaline bases in an amount sufficient to essentially convert said esters into alkaline soaps, (b) said alkaline soaps are separated from said fatty alcohols by extraction to produce a purified fraction of fatty alcohols and an aqueous soap phase, and (c) said soap phase is treated with strong mineral acids in order to release the fatty acids from the soaps.

15 Claims, 2 Drawing Sheets

US 9,045,715 B2

PROCESS FOR PURIFYING CRUDE FATTY ALCOHOLS

CROSS-REFERENCE TO RELATED APPLICATIONS

This application claims priority under 35 U.S.C. §119(e) to U.S. Provisional Application No. 61/485,825, filed May 13, 2011, the disclosure of which is incorporated herein by reference in its entirety.

FIELD OF THE INVENTION

The present invention is related to the area of fatty alcohol production and refers to an improved method for purifying streams of fatty alcohols produced from the respective hydrogenation of fatty acid methyl esters.

BACKGROUND

Fatty alcohols represent important raw materials for various types of consumer products, for example cosmetics and detergents. Typically, they are obtained from vegetable oils for example by transesterification with methanol to form methyl esters and subsequent hydrogenation. The methyl esters for example from coconut or palm kernel oil are typically split into fractions $C_{6-10}$, $C_{12-14}$ and $C_{16-18}$ by distillation in fractionation columns under vacuum. The different fractions are then hydrogenated separately.

In the hydrogenation step the methyl esters are converted to fatty alcohols and methanol. Due to side reactions additional by-products are formed such as for example water, hydrocarbons and wax esters. Furthermore, since the hydrogenation conversion is not 100% complete, residual methyl esters are remaining in the crude fatty alcohol fractions. Obviously, it is desirous to remove these unwanted by-products to a level which is acceptable in terms of the later conversion or application.

On known process involves removing methanol and water from the crude fatty alcohols by stripping in a simple flash distillation unit. In order to separate also other low boilers like hydrocarbons and remaining traces of methanol and water, an additional fractionation in a top cut column is typically applied. For removal of high boilers such as wax esters the fatty alcohols are further fractionated in an overhead distillation column. Alternatively the fatty alcohols can be purified in one column with side stream withdrawal. As a matter of fact, these standard operations require a lot of energy and technical equipment. Also, the waste material, although having a high content of organics, does not have any application and is typically used as an—quite expensive—fuel for generating steam and energy.

DETAILED DESCRIPTION

Figure 1:
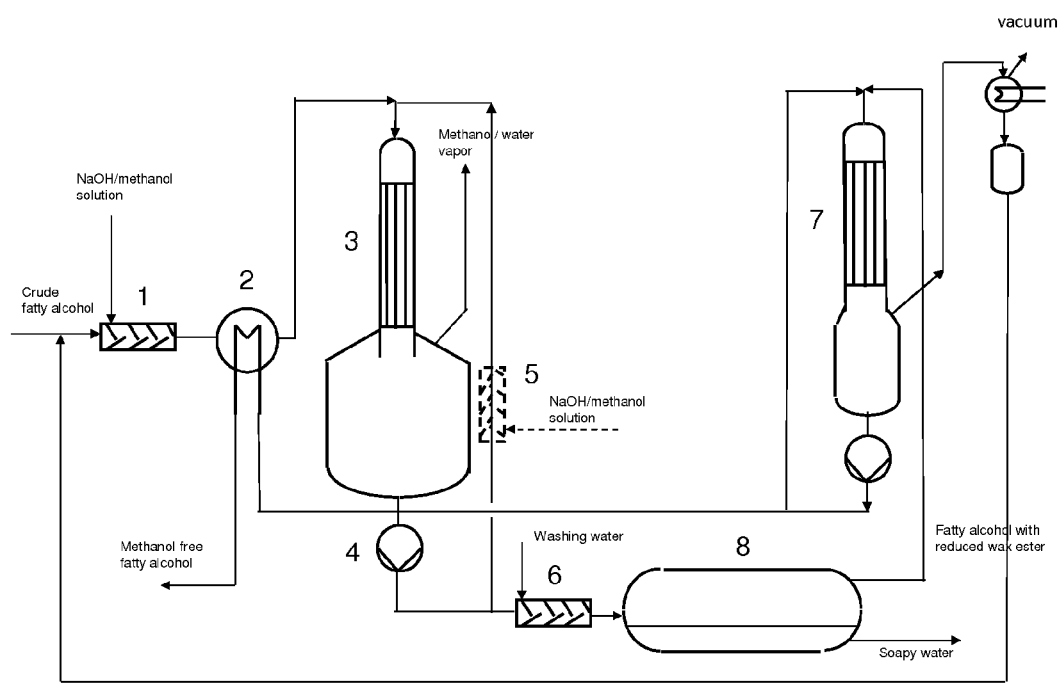
FIG. 1 shows a process for trans-esterification and separation of wax ester and methyl ester from crude fatty alcohols in accordance with one or more embodiments of the present invention.

One or more embodiments of the present invention provide an improved process for the purification of fatty alcohols, in particular for removing esters from the hydrogenated fractions, which is more efficient, easier to handle and less expensive. Simultaneously, the process may provide the unwanted by-products in a quality which can be sold as a valuable product.

One aspect of the present invention pertains to a process for simultaneously purifying fatty alcohols and obtaining a fraction of free fatty acids, wherein:

(a) crude fatty alcohols comprising up to 70, preferably about 1 to about 60, and more preferably about 2 to about 40% b.w. alkyl esters and/or wax esters are treated with alkaline bases in an amount sufficient to essentially convert said esters into alkaline soaps, (b) said alkaline soaps are separated from said fatty alcohols by extraction to produce a purified fraction of fatty alcohols and an aqueous soap phase, and (c) said soap phase is treated with strong mineral acids in order to release the fatty acids from the soaps.

Surprisingly, it has been observed that even huge parts of methyl esters and/or wax esters can be removed from fatty alcohols by transesterification using alkaline bases and forming alkali soaps according to the following equations:

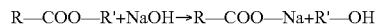

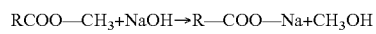

According to one or more embodiments of the present invention, it is possible to reduce the saponification number to a value of at most 0.5, representing a typical specification for fatty alcohols. Compared to what is known from the state of the art and indeed is found in the market, the process is easier to conduct and also more advantageous in terms of energy consumption and the production of a separate phase of free fatty acids, which can be sold as a valuable product rather than to be treated as none-value waste material. In particular, the advantages of some embodiments are:

Increased product yield, since the wax esters are converted to fatty alcohols and alkali soaps. The yield loss is only approximately 50% (w/w) of the wax ester concentration. In the state of the art process the wax esters are completely lost to the distillation residue.

No loss of fatty alcohol via distillation.

Energy reduction due to elimination of the overhead distillation step.

Savings with regard of high pressure steam, cooling water and motive steam for the vacuum unit.

The colour quality of the fatty alcohol is not affected, since the transesterification is performed at low temperature.

Fatty Alcohols

In some embodiments, the fatty alcohols which are subjected to purification are following general formula (I)

in which $R^1$ is a saturated or unsaturated, linear or branched and optionally hydroxyl-substituted hydrocarbon residue with 6 to 36 carbon atoms and 0 or 1 to 5 double bonds. Typical examples are capryl alcohol, caprinyl alcohol, lauryl alcohol, myristyl alcohol, cetyl alcohol, palmoleyl alcohol, stearyl alcohol, cetearyl alcohol, oleyl alcohol, linoly alcohol, linolenyl alcohol, elaidyl alcohol, 12-hydroxy stearyl alcohol, ricinolyl alcohol, gadoleyl alcohol, erucyl alcohol, behenyl alcohol, their mixtures and the technical grade fatty alcohols which can be obtained from renewable oils and fats, like e. g. palm oil, palm kernel oil, coconut oil, olive oil, soy oil, rape seed oil, tallow and fish oil.

In some embodiments, the fatty alcohols which are subjected to purification either comprise:

(i) 12 to 18 carbon atoms and are obtained as the distillate from the hydrogenation of the respective alkyl esters, or (ii) 6 to 36 carbon atoms and are obtained as the distillation bottom from the hydrogenation of the respective alkyl esters.

Typically the crude fatty alcohols comprise 1 to 60% b.w. alkyl esters and/or 5 to 40% b.w. wax esters.

Purification of Fatty Alcohol Distillates

One or more embodiments of the process are illustrated by FIG. 1. As shown in FIG. 1, the crude fatty alcohols from the hydrogenation step may be mixed with alcoholic alkaline bases, preferably NaOH or KOH in methanol in mixing equipments, preferably a static mixer (1), the mixture is preheated via economizer (2) and routed to a first evaporator, preferably a falling film evaporator (3). The reaction of alkyl and/or wax esters with the bases occurs mainly during the heating in economizer and evaporator. Preferably, the evaporator is designed with a large bottom vessel in order to provide the required reaction time of approximately 10 to 30 min. Homogenizing and mixing of the reaction mixture is typically done by a recirculation pump (4). Mixing efficiency can be controlled by adjusting the recirculation rate. As an alternative the alcoholic alkaline solution can be added to the crude fatty alcohol in a static mixer (5), which is installed in the recirculation line. The temperature in the receiving vessel is adjusted to about 80 to about 120, and preferably about 90 to about 110° C. by steam control to the evaporator. The methanol concentration in the bottom product at these temperatures is typically about 5 to about 10% b.w., which is necessary for a good dissolution of alkaline base in the fatty alcohol.

It is also preferred to take off a part of the reaction mixture from the recirculation loop, mixed with water at about 90 to about 120° C. preferably in static mixer (6) and fed to a gravity separator (8), where the mixture splits into a light fatty alcohol phase reduced in wax ester content and a heavy water phase containing the alkaline soaps. The temperature in the separation vessel is preferably about 80 to about 120° C. to enable a good phase separation. The separator is operated typically at about 1 to about 3 barg in order to avoid the evaporation of methanol and water. Depending on the required minimum alkali concentration in the fatty alcohol phase an additional washing step can be performed countercurrently in one or two steps.

Subsequently, the fatty alcohol is taken off from the phase separator as the light phase and is routed to a second evaporator, also preferably a falling film evaporator (7), where the alcohols, e.g. methanol is removed by distillation. The water phase is routed to a soap splitting step for recovery of the fatty acid as described above.

Purification of Fatty Alcohol Residues

Another embodiment of the present invention refers to a process for the purification of high boiling fractions, according to which crude fatty alcohol residues are mixed with alcoholic alkaline bases and subjected to transesterification in a stirred vessel to produce an intermediate transesterification product that is subjected to a two-step distillation to produce a purified stream of fatty alcohols. The residues from the distillation steps are subjected to a treatment with strong mineral acids to obtain the free fatty acids.

Figure 2:
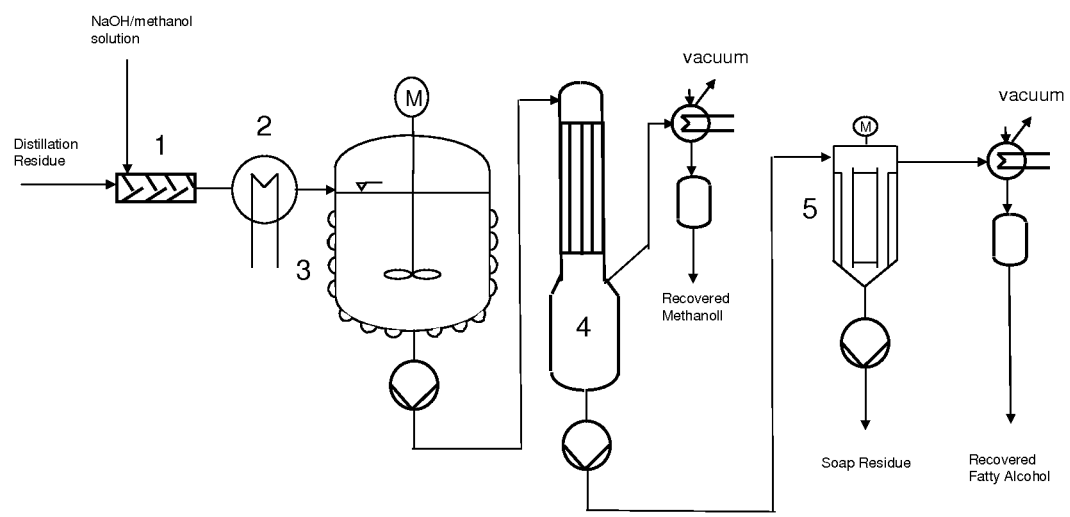
FIG. 2 shows a process for trans-esterification and separation of wax ester and methyl ester from distillation residues in accordance with one or more embodiments of the present invention.

Therefore, an alternative procedure of the invention is saponifying distillation residues from the current fatty alcohol distillations with alkaline bases in methanol or other alcohols in order to split the wax esters contained in the fatty alcohols and distilling the mixture to recover fatty alcohols as set out in FIG. 2. Typically, the distillation residues contain wax esters in the range of about 30 to about 70% b.w., the remainder being mainly fatty alcohols. During saponification with alkaline bases like NaOH or KOH the wax esters are transformed into fatty acid soaps and free fatty alcohols. The reaction mixture may then be supplied to a distillation, preferably a two-step distillation for example in a wiped film evaporator, where the free fatty alcohols are recovered almost quantitatively from the mixture. The loss of fatty alcohols in the soap residue from the evaporator can be kept in the range of about 5 to about 30% b.w.

Preferably, the distillation residue and alcoholic alkaline bases are continuously fed via a static mixer (1) and preheater (2) to a stirred vessel (3), where the transesterification is applied at a temperature of about 120° C. and a residence time of about 30 min. The reaction mixture is then first routed to a methanol stripper (4)—for example a falling film evaporator—where the mixture is distilled at about 500 mbar to atmospheric pressure and finally to a second evaporator, also preferably a wiped film evaporator (5), where the mixture is distilled at a vacuum of about 1 to about 10 mbar and temperatures up to about 250° C. The recovered fatty alcohols are condensed and the alkaline soaps are discharged from the evaporator as residue.

Soap Splitting

The liberation of the free fatty acids from their alkaline soaps can be conducted according to the state of the art, for example by treating the aqueous solution with strong mineral acids like sulphuric acid or hydrochloric acid. It is also possible to use any other organic acid that is strong enough to replace the fatty acids in their salts. Once the splitting has taken place, the crude fatty acids are washed with water and separated from the aqueous phase by gravity settling.

EXAMPLES

Example 1

100 g of $C_{12}/C_{14}$ fatty alcohol with saponification number 0.88 and wax ester content of 0.51% (w/w) were mixed with 14 g 0.1 mol/l NaOH in methanol and heated in a flask for 60 min at 85° C. under reflux. Methanol was then removed by distillation in a rotary evaporator. After that 20 g of deionised water were added and the product was washed in the rotavapor for 30 min at 80° C. The mixture was then decanted in a separating funnel and the organic phase dried in the rotary evaporator. The resulting saponification number of the organic phase was 0.38 and wax ester content 0.26% (w/w). Measured sodium content in the organic phase was 150 ppm and 1,700 ppm in the aqueous phase.

Example 2

100 g $C_{12}/C_{14}$ fatty alcohol with a saponification number of 0.88 and wax ester content of 0.51% (w/w) were mixed with 14 g 0.1 mol/l KOH in methanol and heated in a flask for 60 min at 85° C. under reflux. Methanol was then removed with a rotary evaporator. Afterwards 20 g deionised water was added and the product was washed for 30 min at 80° C. in the rotary evaporator. The mixture was then decanted in a separating funnel. After phase separation the organic phase was dried in the rotary evaporator. Resulting saponification number was 0.38 and wax ester content 0.25% (w/w). Measured potassium content was 330 ppm in the organic phase and 2,800 ppm in the aqueous phase.

Example 3

100 g of a distillation residue containing 6% b.w. methyl ester, 34% b.w. wax ester and 60% b.w. free fatty alcohol was mixed with 120 g 0.1 mol/l NaOH in methanol and reacted for 30 min at 120° C. in an autoclave. Subsequently, methanol was distilled from the mixture in a rotary evaporator at 130° C. and atmospheric pressure. The resulting mixture had a residual methanol content of 1.1% (w/w). The mixture was then fed to a wiped film evaporator at 1 mbar and 235° C. 71 g distillate was achieved containing 1.6% methanol, the rest free fatty alcohols. The remaining 35 g of residue still contained 26.2% (w/w) free fatty alcohol.

The invention claimed is:

1. A process for simultaneously purifying fatty alcohols and obtaining a fraction of free fatty acids, the process comprising:
   (a) treating crude fatty alcohols comprising up to 70% b.w. $C_{6-18}$ fatty acid methyl esters and/or wax esters with alkaline bases in an amount sufficient to essentially convert said esters into alkaline soaps,
   (b) separating said alkaline soaps from said fatty alcohols by extraction to produce a purified fraction of fatty alcohols and an aqueous soap phase, and
   (c) treating said soap phase with strong mineral acids to release the fatty acids from the soaps.

2. The process of claim 1, wherein fatty alcohols have the following general formula (I)

$$R^1OH \qquad (I)$$

in which $R^1$ is a saturated or unsaturated, linear or branched and optionally hydroxyl-substituted hydrocarbon residue with 6 to 18 carbon atoms and up to 5 double bonds.

3. The process of claim 1, wherein said fatty alcohols in (a) comprise 12 to 18 carbon atoms and are obtained as the distillate from the hydrogenation of the respective fatty acid methyl esters.

4. The process of claim 1, wherein said fatty alcohols in (a) comprise 6 to 18 carbon atoms and are obtained as the distillation bottom from the hydrogenation of the respective fatty acid methyl esters.

5. The process of claim 1, wherein said crude fatty alcohols comprise 1 to 60% b.w. fatty acid methyl esters and/or 5 to 40% b.w. wax esters.

6. The process of claim 1, wherein said purification of the crude fatty alcohols according to step (a) leads to a fraction of purified fatty alcohols showing a saponification number of at most 0.5.

7. The process of claim 1, wherein said crude fatty alcohol in (a) are mixed with alcoholic alkaline bases and subjected to transesterification in an evaporator.

8. The process of claim 7, wherein said evaporator is a falling-film evaporator.

9. The process of claim 7, wherein said evaporator is operated at a temperature of from 80 to 170° C.

10. The process of claim 7, wherein a first part of the reaction product leaving the evaporator is recycled and fed to the top of the evaporator.

11. The process of claim 10, wherein a second part of the reaction product leaving the evaporator is mixed with water and fed to a gravity separator, where the mixture is separated into a first light fatty alcohol phase and a heavy water phase containing the alkaline soaps.

12. The process of claim 11, wherein said light fatty alcohol phase is subjected to a distillation in a second evaporator in order to remove remaining alcohols, while said heavy water phase is subjected to a treatment with strong mineral acids to obtain the free fatty acids.

13. The process of claim 4, wherein said crude fatty alcohol residues are mixed with alcoholic alkaline bases and subjected to transesterification in a stirred vessel to produce an intermediate transesterification product that is subjected to a two-step distillation to finally produce a purified stream of fatty alcohols.

14. The process of claim 13, wherein the residues of the distillation steps, containing the fatty acid soaps, are subjected to treatment with strong mineral acids to obtain the free fatty acids.

15. The process of claim 14, wherein said mineral acids are selected from the group consisting of sulphuric acid and hydrochloric acid.

* * * * *